United States Patent
Franz et al.

(10) Patent No.: US 9,526,740 B2
(45) Date of Patent: Dec. 27, 2016

(54) PROCHELATORS AS BROAD-SPECTRUM ANTIMICROBIAL AGENTS AND METHODS OF USE

(71) Applicant: Duke University, Durham, NC (US)

(72) Inventors: Katherine J. Franz, Durham, NC (US); Dennis J. Thiele, Chapel Hill, NC (US); Marian Helsel, Durham, NC (US); Richard Festa, North Chesterfield, VA (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 15/094,349

(22) Filed: Apr. 8, 2016

(65) Prior Publication Data

US 2016/0220592 A1 Aug. 4, 2016

Related U.S. Application Data

(63) Continuation of application No. 14/213,207, filed on Mar. 14, 2014, now Pat. No. 9,333,213.

(60) Provisional application No. 61/789,720, filed on Mar. 15, 2013.

(51) Int. Cl.
*A61K 31/69* (2006.01)
*A61K 31/40* (2006.01)
*A61K 31/435* (2006.01)

(52) U.S. Cl.
CPC ............. *A61K 31/69* (2013.01); *A61K 31/40* (2013.01); *A61K 31/435* (2013.01)

(58) Field of Classification Search
CPC ....... A61K 31/69; A61K 31/40; A61K 31/435
See application file for complete search history.

(56) References Cited

U.S. PATENT DOCUMENTS 8,551,976 B2  10/2013  Franz et al.
2013/0096085 A1  4/2013  Franz et al.

OTHER PUBLICATIONS

Dickens MG and Franz KJ. A prochelator activated by hydrogen peroxide prevents metal-induced amyloid beta aggregation. Chembiochem. Jan. 4, 2010; 11(1): 59-62.

Festa RA et al. Exploiting innate immune cell activation of a copper-dependent antimicrobial agent during infection. Chem Biol. Aug. 14, 2014; 21(8): 977-987.

*Primary Examiner* — Yong Chong
(74) *Attorney, Agent, or Firm* — Myers Bigel, P.A.

(57) ABSTRACT

The present disclosure provides methods of treating (including ameliorating and/or preventing) pathogenic infections by administering a therapeutically effective amount of a prochelator. The present disclosure further provides pharmaceutical compositions and a kit comprising the prochelator therein.

18 Claims, 8 Drawing Sheets

PROCHELATORS AS BROAD-SPECTRUM ANTIMICROBIAL AGENTS AND METHODS OF USE

RELATED APPLICATIONS

This application is a continuation of U.S. patent application Ser. No. 14/213,207, filed Mar. 14, 2014, now allowed, which claims the benefit of U.S. Provisional Patent Application Ser. No. 61/789,720, filed Mar. 15, 2013, the disclosure of each of which is incorporated by reference herein in its entirety.

STATEMENT OF GOVERNMENT SUPPORT

This invention was made with Government Support under Grant Nos.: 1RO1-GM084176-01 and GM41840 from the National Institutes of Health. The US Government has certain rights to this invention.

BACKGROUND

A critical response of the innate immune system to microbial infection is the ingestion, destruction and clearance of pathogens by activated phagocytic cells. Within their phagosomal compartments, macrophages generate an environment that is hostile to microbes via the production of reactive oxygen and nitrogen species, the elaboration of proteases, acidification of the phagosomal lumen and the export of iron.[1,2] Unlike iron, copper (Cu) is not essential for many pathogens, although it is an essential trace element for mammals. In fact, Cu has been used for over a century as a microbiocidal agent for the elimination of human and plant pathogens.[3] Moreover, Cu is critical for normal innate immune cell function and Cu deficiency in mammals renders the host susceptible to microbial pathogens. It is well documented that Cu levels rise dramatically in the serum of mammals during infection/inflammation and Cu accumulates at sites of inflammation, underscoring a specialized role for Cu in innate immunity.[4,5] Consistent with a microbiocidal role for Cu in macrophages, phagosomal Cu concentrations rise dramatically in activated macrophages in parallel with increased expression of the Ctr1 plasma membrane Cu importer and the Atp7A Cu pump on the phagosomal membrane.[6,7] Moreover, studies in both prokaryotic and fungal pathogens demonstrate the requirement for the Cu homeostasis machinery in resistance to macrophage killing.[7,8] Together, these studies provide compelling evidence for a critical role of Cu in microbiocidal activity of the host, which is countered by the Cu homeostasis machinery of invading bacterial and fungal pathogens.

Biocidal properties of Cu have been documented since ancient Egyptians used it for water and wound sterilization in 2400 B.C.[9] The Bordeaux mixture of copper sulfate and lime has been used since 1880 as a fungicide for grapes and other plants,[3] while metallic Cu surfaces, which likely release Cu ions upon bacterial contact, may reduce contamination in hospitals.[10-12] Metallic Cu, Cu salts, and Cu compounds continue to be used to control bacterial, fungal, and algal growth in agricultural and healthcare settings where microbes exist in the environment.[3] The environment of pathogenic microbes, however, is ultimately the infected host, and while Cu and its complexes have been used for so long as environmental antimicrobials, no approach to date has been effective at using Cu to fight infection in a mammalian host. A challenge in this area is to discover ways to deliver or reallocate Cu selectively to the site of infection or inflammation.[4]

SUMMARY OF THE INVENTION

The present disclosure provides an innovative approach that harnesses the chemistry of Cu along this host/pathogen interface to create new broad-spectrum antimicrobials against both bacterial and fungal pathogens.

One aspect of the present disclosure provides methods of treating (including but not limited to ameliorating and/or preventing) pathogenic infections in a subject comprising, consisting of, or consisting essentially of administering to the subject in need thereof a therapeutically effective amount of a prochelator such that the infection is treated, ameliorated and/or prevented.

In some embodiments, the prochelator comprises quinolone boronic ester (OBP), derivatives thereof and salts thereof.

In some embodiments, the pathogen comprises a fungal pathogen. In some embodiments, the fungal pathogen comprises a yeast. In certain embodiments, the fungal pathogen comprises *C. neoformans*.

In other embodiments, the pathogen comprises a bacterial pathogen. In some embodiments, the bacterial pathogen comprises a gram-negative bacteria. In certain embodiments, the gram-negative bacteria comprises *E. coli*. In other embodiments, the bacterial pathogen comprises a gram-positive bacteria. In certain embodiments, the gram-positive bacteria comprise *S. aureus*. In some embodiments, the gram-positive bacteria comprises a *mycobacterium*. In some embodiments, the mycobacteria comprise *M. tuberculosis*. In some embodiments, the mycobacteria compris *M. marinum*. In some embodiments, the *mycobacterium* comprise *M. leprae*.

In yet another embodiment, the prochelator is administered at the onset of disease. In other embodiments, the prochelator is administered prior to disease symptoms. In yet other embodiments, the prochelator is administered after the onset of disease symptoms.

In some embodiments, the subject comprises a mammal. In certain embodiments, the mammal comprises a human being.

Another aspect of the present disclosure comprises a pharmaceutical composition comprising, consisiting of or consisiting essentially of a prochelator according to the present disclosure and a pharmaceutically acceptable carrier.

Yet another aspect of the present disclosure provides a kit comprising, consisting of, or consisting essentially of a prochelator capable of treating, preventing and/or ameliorating pathogenic infections in accordance with the present disclosure and instructions for use.

Yet another aspect of the present disclosure provides for all that is disclosed and illustrated herein.

BRIEF DESCRIPTION OF THE DRAWINGS

The foregoing aspects and other features of the invention are explained in the following description, taken in connection with the accompanying drawings, wherein.

DETAILED DESCRIPTION OF THE INVENTION

Figure 1:
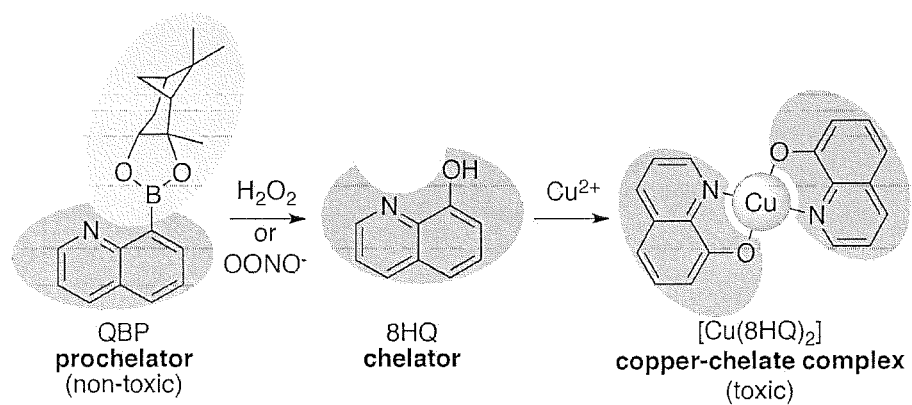
FIG. 1 is a schematic showing the prochelator reaction. The prochelator QBP contains an aryl boronic ester masking group that blocks metal binding but is released upon reaction with $H_2O_2$ or OONO— to give the metal chelating agent 8-hydroxyquinoline (8HQ) (and non-toxic boric acid and pinanediol, not shown). Macrophage activation in response to infection stimulates Cu uptake and generates an oxidative burst that includes $H_2O_2$ and OONO—, thereby providing chemical signals from the immune system to convert a non-toxic prochelator into a microbicidal Cu-chelate complex.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

One aspect of the present disclosure provides a method of treating, ameliorating and/or preventing pathogenic infections in a subject comprising, consisting of, or consisting essentially of administering to the subject in need thereof a therapeutically effective amount of a prochelator such that the infection is treated, ameliorated and/or prevented.

As used herein, the term "subject" is intended to include human and non-human animals. Exemplary human subjects include a human patient suffering from a pathogentic infection, such as one that is caused by a bacterial pathogen, e.g., E. coli. The term "non-human animals" includes all vertebrates, e.g., non-mammals (such as chickens, amphibians, reptiles) and mammals, such as non-human primates, domesticated and/or agriculturally useful animals (such as sheep, dogs, cats, cows, pigs, etc.), and rodents (such as mice, rats, hamsters, guinea pigs, etc.).

As used herein, the term "pathogenic infections" refers to any infections caused by either a fungal pathogen or a bacterial pathogen. In some embodiments, the fungal pathogen comprises a yeast. Examples include, but are not limited to, *C. neoformans, C. albicans, C. tropicalis, C. stellatoidea, C. glabrata, C. krusei, C. parapsilosis, C. guilliermondii, C. viswanathii, C. lusitaniae*, and *Rhodotorula mucilaginosa*. In certain embodiments, the fungal pathogen comprises *C. neoformans*. In other embodiments, the pathogen comprises a bacterial pathogen. In some embodiments, the bacterial pathogen comprises a gram-negative bacteria. Examples include, but are not limited to, *E. coli, Salmonella, Shigella*, Enterobacteriaceae, *Pseudomonas, Moraxella, Helicobacter, Stenotrophomonas*, Bdellovibrio, acetic acid bacteria, *Legionella, Neisseria gonorrhoeae, Neisseria meningitidis), Moraxella catarrhalis*, Hemophilus *influenzae, Helicobacter pylori* and *Acinetobacter baumannii*. In certain embodiments, the gram-negative bacteria comprises *E. coli*. In other embodiments, the bacterial pathogen comprises a gram-positive bacteria. Examples include, but are not limited to, *Mycobacterium, C. diphtheriae, N. asteroides, S. aureus, S. pneumoniae, S. somaliensis* and *S. sudanensis*. In certain embodiments, the gram-positive bacteria comprise *S. aureus*. In some embodiments, the gram-positive bacteria comprises a *Mycobacterium*. In some embodiments, the mycobacteria comprise *M. tuberculosis*. In some embodiments, the mycobacteria compris *M. marinum*. In some embodiments, the *mycobacterium* comprise *M. leprae*.

As used herein, the term "prochelator" refers to those compounds that convert to chelator and increase their affinity for metal ions in response to a stimulus where the stimulus includes reactive species of the oxidative burst of an infected macrophage. Examples of such compounds include, but are not limited to, quinolone boronic ester (QBP) (see, e.g., U.S. patent application Ser. No. 13/386,441 "Prochelators Useful for Inhibiting Metal-Associated Toxicity", the contents of which are hereby incorporated by reference in its entirety), 2-boronobenzaldehyde isonicotinoyl hydrazone (SIH-B) (see, e.g., Wei, Y et al 2007 Angew Chem Int Ed Engl. 46(25): 4722-4725, the contents of which are hereby incorporated by reference in its entirety), and (4-(5-(2-((4-boronobenzyl)oxy)phenyl)-3-(2-hydroxyphenyl)-1H-1,2,4-triazol-1-yl)benzoic acid) (TIP) (see, e.g., Kielar F et al 2012 Inorganica Chimica Acta 393: 294-303, the contents of which are hereby incorporated by reference in its entirety), combinations thereof. In certain embodiments, the prochelator comprises QBP.

As used herein, the terms "treat", "ameliorate" and "prevent" are not intended to be absolute terms. Treatment can refer to any reduction in the frequency or severity of symptoms, improvement in patient comfort and/or function, etc. The effect of treatment can be compared to an individual or pool of individuals not receiving a given treatment, or to the same patient prior to, or after cessation of treatment. In some aspects, the severity of infection is reduced by at least 10%, as compared, e.g., to the individual before administration or to a control individual not undergoing treatment. In some aspects the severity of infection is reduced by at least 25%, 50%, 75%, 80%, or 90%, or in some cases, no longer detectable using standard diagnostic techniques. The term "ameliorate" refers to a complete removal of a pathogenic infection. As indicated above, the amelioration may be of difference level, for example, such that the pathogenic infection is made better or healed or such that fewer sympotoms are observed than would likely occur absent treatment. The term "prevent" refers to the prevention of infection in a subject by a bacterial pathogen and thereby no subject will not suffer any symptoms of infection. As indicated above, the prevention may be complete (no detectable symptoms) or partial, such that fewer symptoms are observed than would likely occur absent treatment.

As used herein, the term "therapeutically effective" refers to a dosage of a prochelator as described herein (e.g., a quinoline boronic ester) that is effective for eliciting a desired effect. This term as used herein may also refer to an amount effective at bringing about a desired in vivo effect in an animal, mammal, or human, such as reducint pathogenic infection and the like. A therapeutically effective amount may be administered in one or more adminstrations (e.g., the compound may be given as a preventative treatment or therapeutically at any stage of disease progression, before or after symptoms, and the like), applications or dosages and is not intended to be limited to a particular formulation, combination or administration route. It is within the scope of the present disclosure that the prochelator as described herein (e.g., a quinoline boronic ester) may be administered at various times during the course of infection in the subject. The times of administration and dosages used will depend on several factors, such as the goal of treatment (e.g., treating v. ameliorating v. preventing), condition of the subject, etc. and can be readily determined by one skilled in the art. For example, in one embodiment the prochelator as described herein (e.g., a quinoline boronic ester) is administered at the onset of infection. In other embodiments, the prochelator as described herein (e.g., a quinoline boronic ester) is administered after onset of the infection. In yet other embodiments, the prochelator as described herein (e.g., a quinoline boronic ester) is administered prior to the onset of infection.

The term "administration" or "administering," as used herein, refers to providing, contacting, and/or delivery of a prochelator as described herein (e.g., quinoline boronic ester) by any appropriate route to achieve the desired effect. These compounds may be administered to a subject in numerous ways including, but not limited to, orally, ocularly, nasally, intravenously, topically, as aerosols, suppository, etc. and may be used in combination.

"Transition metal" as used herein refers to one of the 38 elements in groups 3 through 12 of the periodic table. In certain embodiments, the transition metals of this invention include, but are not limited to: scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, etc.

"Alkyl" as used herein alone or as part of another group, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "akyl" or "loweralkyl" is intended to include both substituted and unsubstituted alkyl or loweralkyl unless otherwise indicated and these groups may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkylene bridge" as used herein refers to a straight or branched chain hydrocarbon bridging species containing from 1 to 10 carbon atoms. Representative examples include, but are not limited to, C1-C5 bridges such as —(CH$_2$)$_n$— where n is 1 or 2 to 3, 4 or 5. The term "alkylene bridge" is intended to include both substituted and unsubstituted unless otherwise indicated and may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, halo alkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkenyl" as used herein alone or as part of another group, refers to a straight or branched chain hydrocarbon containing from 1 to 10 carbon atoms (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkynyl" as used herein alone or as part of another group, refers to a straight or branched chain hydrocarbon containing from 1 to 10 carbon atoms (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralknynyl unless otherwise indicated and these groups may be substituted with the same groups as set forth in connection with alkyl and loweralkyl above.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. Bicyclic and tricyclic ring systems are also included. These rings may be optionally substituted with additional substituents as described herein such as halo or loweralkyl. The term "cycloalkyl" is generic and intended to include heterocyclic groups as discussed below unless specified otherwise.

"Heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. In some embodiments aryl contains a "hetero" atom and is also a "heterocyclo" group as described above. The term "aryl" is intended to include both substituted and unsubstituted aryl unless otherwise indicated and these groups may be substituted with the same groups as set forth in connection with alkyl and loweralkyl above. More specifically, "aryl" groups as used herein may be substituted 1, 2, 3, or 4 or more times with independently selected halo (e.g., haloaryl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Heteroaryl" as used herein is as described in connection with heterocyclo above.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Halo" as used herein refers to any suitable halogen, including —F, —Cl, —Br, and —I.

"Mercapto" as used herein refers to an —SH group.

"Azido" as used herein refers to an —N$_3$ group.

"Cyano" as used herein refers to a —CN group.

"Formyl" as used herein refers to a —C(O)H group.

"Carboxylic acid" as used herein refers to a —C(O)OH group.

"Hydroxyl" as used herein refers to an —OH group.

"Diol" as used herein refers to a chemical compound containing two hydroxyl groups.

"Nitro" as used herein refers to an —NO$_2$ group.

"Acyl" as used herein alone or as part of another group refers to a —C(O)R radical, where R is any suitable substituent such as aryl, alkyl, alkenyl, alkynyl, cycloalkyl or other suitable substituent as described herein.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Amino" as used herein means the radical —NH$_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —NR$_a$R$_b$, where R$_a$ and R$_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —NR$_a$R$_b$, where R$_a$ is an acyl group as defined herein and R$_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Amide" as used herein alone or as part of another group refers to a —C(O)NR$_a$R$_b$ radical, where R$_a$ and R$_b$ are any suitable substituent such as alkyl, cycloalkyl, alkenyl, alkynyl or aryl.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Sulfonamide" as used herein alone or as part of another group refers to a —S(O)$_2$NR$_a$R$_b$ radical, where R$_a$ and R$_b$ are any suitable substituent such as H, alkyl, cycloalkyl, alkenyl, alkynyl or aryl.

"Urea" as used herein alone or as part of another group refers to an N(R$_c$)C(O)NR$_a$R$_b$ radical, where R$_a$, R$_b$ and R$_c$ are any suitable substituent such as H, alkyl, cycloalkyl, alkenyl, alkynyl or aryl.

"Alkoxyacylamino" as used herein alone or as part of another group refers to an —N(R$_a$)C(O)OR$_b$ radical, where R$_a$, R$_b$ are any suitable substituent such as H, alkyl, cycloalkyl, alkenyl, alkynyl or aryl.

"Aminoacyloxy" as used herein alone or as part of another group refers to an —OC(O)NR$_a$R$_b$ radical, where R$_a$ and R$_b$ are any suitable substituent such as H, alkyl, cycloalkyl, alkenyl, alkynyl or aryl.

Prochelator Active Compounds

As noted above, examples Prochelators useful for carrying out the present invention include, but are not limited to, those described in Franz and Leed, U.S. patent application Ser. No. 13/386,441 "Prochelators Useful for Inhibiting Metal-Associated Toxicity," (published as US Patent Application Pub. No. US 2013/0096085), the contents of which are hereby incorporated by reference in its entirety. Thus active compounds of the present invention include, but are not limited to, compounds of Formula I and Formula II:

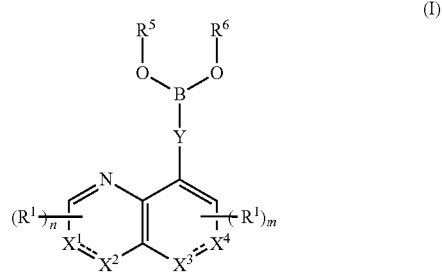

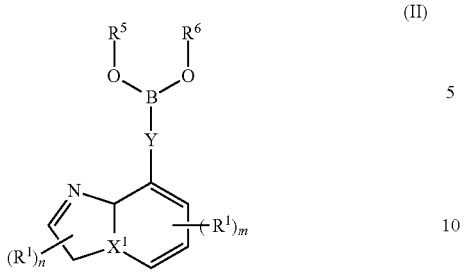
(II)

wherein:
Y is a covalent bond or —O—R⁷-R⁸—, where $R^7$ is —CH$_2$— or —CO$_2$CH$_2$— and $R^8$ is phenylene (unsubstituted or optionally substituted), which phenylene is preferably unsubstituted or substituted 1, 2, 3 or 4 times with independently selected halo or alkyl;

n and m are each an integer from 1 to 3;

each $R^1$ is independently selected from the group consisting of: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy;

$R^5$ and $R^6$ are independently selected H, alkyl, or haloalkyl, or together form an alkylene bridge, which alkylene bridge may be unsubstituted or substituted from 1 to 4 times with alkyl, halo, a fused cycloalkyl or a fused aryl ring;

each X is independently selected from the group consisting of N, O, and CH; and dashed lines represent optional double bonds;

or a pharmaceutically acceptable salt or prodrug thereof.

In some embodiments of Formula I and Formula II, $R^5$ and $R^6$ are independently selected H, alkyl, or haloalkyl.

In some embodiments of Formula I and Formula II, $R^5$ and $R^6$ together form an alkylene bridge, which alkylene bridge may be unsubstituted or substituted from 1 to 4 times with alkyl, halo, a fused cycloalkyl or a fused aryl ring.

In some embodiments of Formula I and Formula II, $R^5$ and $R^6$ together form a C2 alkylene bridge having a bicyclic cycloalkyl substituted thereon, which bicyclic cycloalkyl may be unsubstituted or substituted from 1 to 4 times with alkyl or halo.

In some embodiments of Formula I and Formula II, $R^5$ and $R^6$ together form a group:

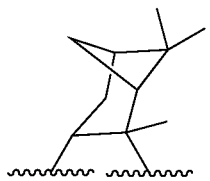 [SMILES: *C1CC2CC(C1(*)C)C2(C)C]

In some embodiments, the compound of Formula I is compound of Formula Ia, Formula Ib. Formula Ic. Formula Id. Formula Ie. or Formula If:

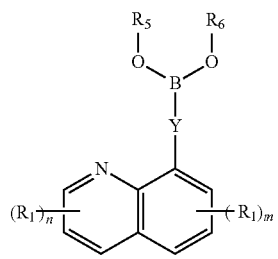
(Ia)

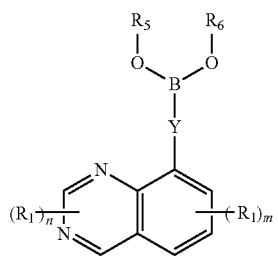
(Ib)

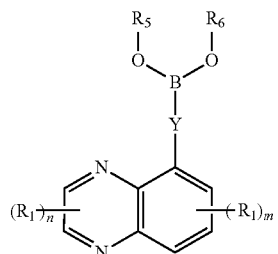
(Ic)

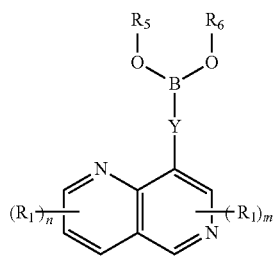
(Id)

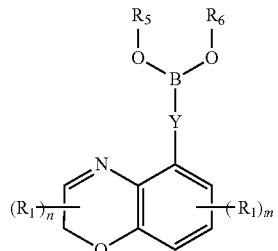
(Ie)

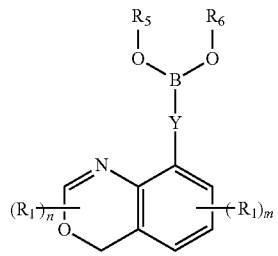
(If)

wherein:
Y is a covalent bond or —O—R⁷-R⁸—, where $R^7$ is —CH$_2$— or —CO$_2$CH$_2$— and $R^8$ is phenylene, which phenylene is unsubstituted or substituted 1, 2, 3 or 4 times with independently selected halo or alkyl;

n and m are each an integer from 1 to 3;

each $R^1$ is independently selected from the group consisting of: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy; and $R^5$ and $R^6$ are independently selected H, alkyl, or haloalkyl, or together form an alkylene bridge, which alkylene bridge may be unsubstituted or substituted from 1 to 4 times with alkyl, halo, a fused cycloalkyl or a fused aryl ring;

or a pharmaceutically acceptable salt or prodrug thereof.

In some embodiments of Formula Ia, Formula Ib, Formula Ic, Formula Id, Formula Ie, or Formula If, $R^5$ and $R^6$ are independently selected H, alkyl, or haloalkyl.

In some embodiments of Formula Ia, Formula Ib, Formula Ic, Formula Id, Formula Ie, or Formula If, $R^5$ and $R^6$ together form an alkylene bridge, which alkylene bridge may be unsubstituted or substituted from 1 to 4 times with alkyl, halo, cycloalkyl (e.g., a bicyclic cycloalkyl), or a fused aryl ring.

In some embodiments of Formula I, $R^5$ and $R^6$ together form a C2 alkylene bridge having a bicyclic cycloalkyl substituted thereon, which alkylene bridge and/or bicyclic cycloalkyl may be unsubstituted or substituted from 1 to 4 times with alkyl or halo.

In some embodiments of Formula Ia, Formula Ib, Formula Ic, Formula Id, Formula Ie, or Formula If, $R^5$ and $R^6$ together form a group:

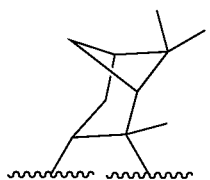 [SMILES: *C1CC2CC(C1(*)C)C2(C)C]

In some embodiments of Formula Ia, the active compound is a compound:

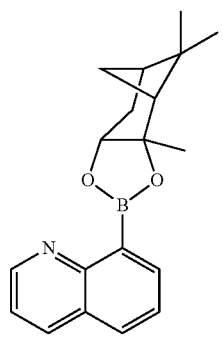 [SMILES: CC1(C)C2CC3OB(c4cccc5cccnc45)OC3(C)C1C2]

or a pharmaceutically acceptable salt or prodrug thereof.

Additional examples of active compounds useful in the present invention include, but are not limited to, those chelators and prochelators described Franz and Charkoudian, U.S. Pat. No. 8,236,783, and Franz and Kielar, U.S. Pat. No. 8,551,976, the disclosures of which are incorporated by reference herein in their entirety.

Pharmaceutical Compositions

In certain embodiments, the prochelator as described herein (e.g., a quinoline boronic ester) may be in the form of a pharmaceutical compositon. As used herein, the term "pharmaceutical composition" refers to the combination of compound (i.e., for example, quinoline boronic ester) with a carrier, inert or active, making the composition especially suitable for diagnostic or therapeutic use in vivo, in vivo or ex vivo. A "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. (1975)).

As used herein, the term "pharmaceutically acceptable salt" refers to any pharmaceutically acceptable salt (e.g., acid or base) of a compound of the present disclosure which, upon administration to a subject, is capable of providing a compound of this invention or an active metabolite or residue thereof. "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like. Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as Na$^+$, NH$_4^+$, and NW$_4^+$ (wherein W is a C$_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Other embodiments of the present disclosure provides kits for treating, ameliorating and/or preventing a pathogenic infection in a subject. In some embodiments, the kit comprises, consists of, or consists essentially of a prochelator, such as quinolone boronic ester (QBP), and instructions for use Dosage and Routes of Administration.

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The therapeutically effective dosage of any one active agent, the use of which is in the scope of present invention, will vary somewhat from compound to compound, and patient to patient, and will depend upon factors such as the age and condition of the patient and the route of delivery. Such dosages can be determined in accordance with routine pharmacological procedures known to those skilled in the art. As a general proposition, a dosage from about 0.1 or 1.0 to about 250 or 500 mg/kg will have therapeutic efficacy, with all weights being calculated based upon the weight of the active compound, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 10 mg/kg to about 200 mg/kg may be employed for oral administration. Typically, a dosage from about 1 mg/kg to 100 mg/kg may be employed for intramuscular injection. The duration of the treatment is usually once per day for a period of two to three weeks or until the condition is essentially controlled. Lower doses given less frequently can be used prophylactically to prevent or reduce the incidence of recurrence of the disease.

The following examples are offered by way of illustration and not by way of limitation.

EXAMPLES

1. Prochelator Approach. The approach disclosed here is innovative because it exploits the unique chemical milieu created by the host in response to infection to mobilize endogenous Cu to exacerbate microbial killing. The molecules used in this approach are prochelators, which by our definition are agents that increase their affinity for metal ions in response to a stimulus. The prochelator concept is shown in FIG. 1, where the stimulus includes reactive species of the oxidative burst of an infected macrophage.

The lead compound in this work is the quinoline boronic ester QBP (see FIG. 1), which is the subject of U.S. patent application Ser. No. 13/386,441 ("Prochelators Useful for Inhibiting Metal-Associated Toxicity,"). Here we disclose the application of this molecule as a broad-spectrum antimicrobial agent. Most of the data collected to date are from experiments using *Cryptococcus neoformans*, an opportunistic pathogen that primarily infects immunocompromised individuals via inhalation and can ultimately cause lethal meningoencephalitis.[13, 14] Treatment with current antifungal drugs is limited by host toxicity, highlighting the significance of our work to identify Cu agents as new antifungal therapies. The approach may be generally applicable to other fungal and bacterial pathogens.

2. Chelator 8HQ is Fungicidal in the Presence of Copper. 8HQ, also called oxine, has a long history of antifungal, antibacterial, and other biological effects associated with its metal binding ability.[15-17] 8HQ comprises the core of the topical antiseptic and oral antibiotic drug clioquinol, which was banned in the 1970s but has resurfaced as a potential drug for Alzheimer's disease.[18] While hydroxyquinolines have appealing biological effects, they also have severe drawbacks[19, 20] and are cytotoxic to mammalian cells in culture.[21,22]

Figure 2:
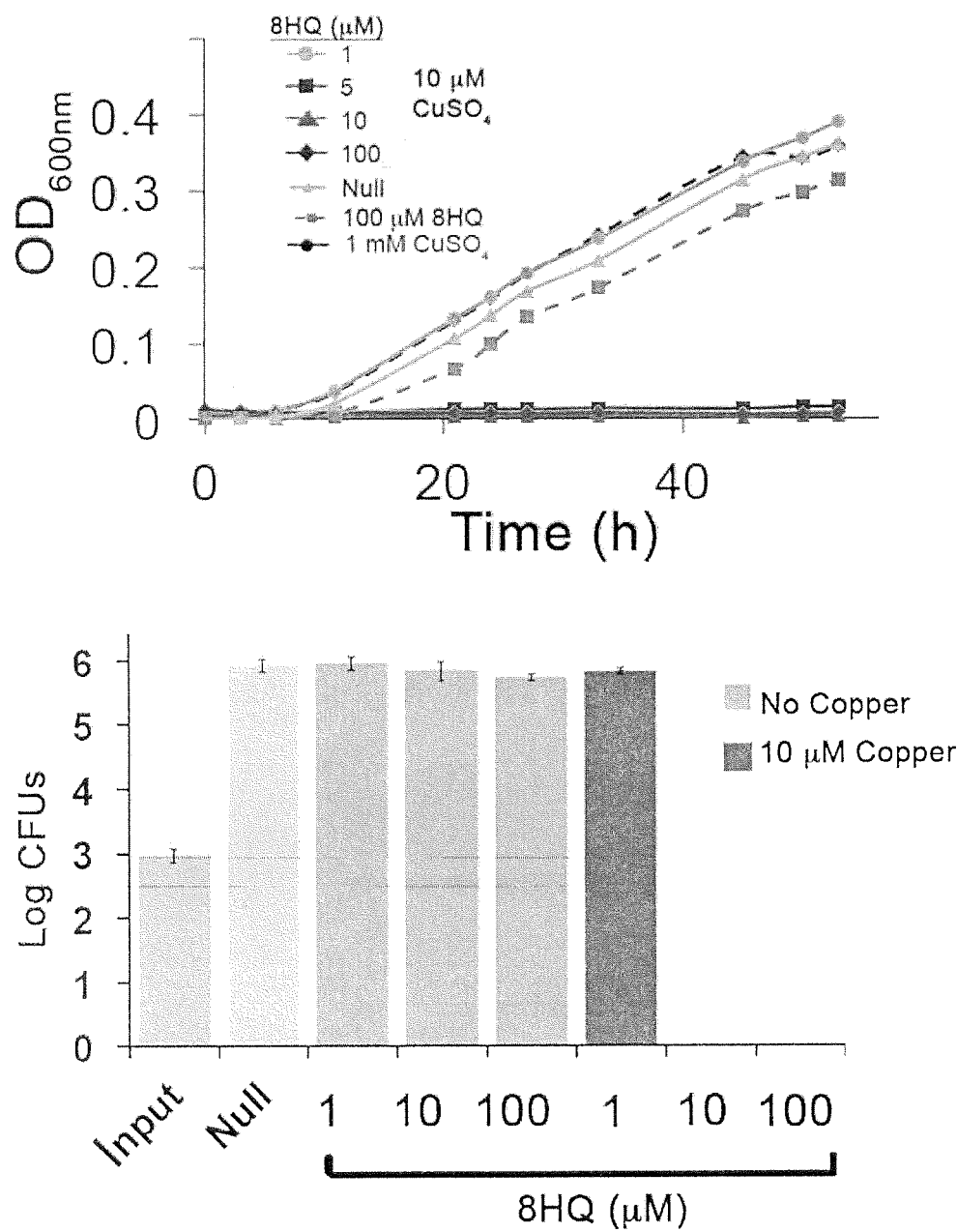
FIG. 2 is a graph showing that 8HQ inhibited growth of C. neoformans in a Cu-dependent manner. Top: Growth of C. neoformans H99 strain in SC media monitored by optical density (OD) over the course of 50 hours, where an increase in $OD_{600}$ indicates normal growth. C. neoformans growth is not affected by 100 μM 8HQ or even by 1 mM copper when tested individually, but the combination of 8HQ and CuSO4 completely inhibits growth with a mimimal inhibitory concentration (MIC) ~5 μM 8HQ with 10 μM Cu. Bottom: In a follow up experiment to the growth curve assay shown on top, samples were taken after 50 h and plated to determine colony-forming units (CFUs). The absence of CFUs for samples containing 10 μM or higher 8HQ in the presence of 10 μMCuSO4 indicates a fungicidal response.
Figure 3:
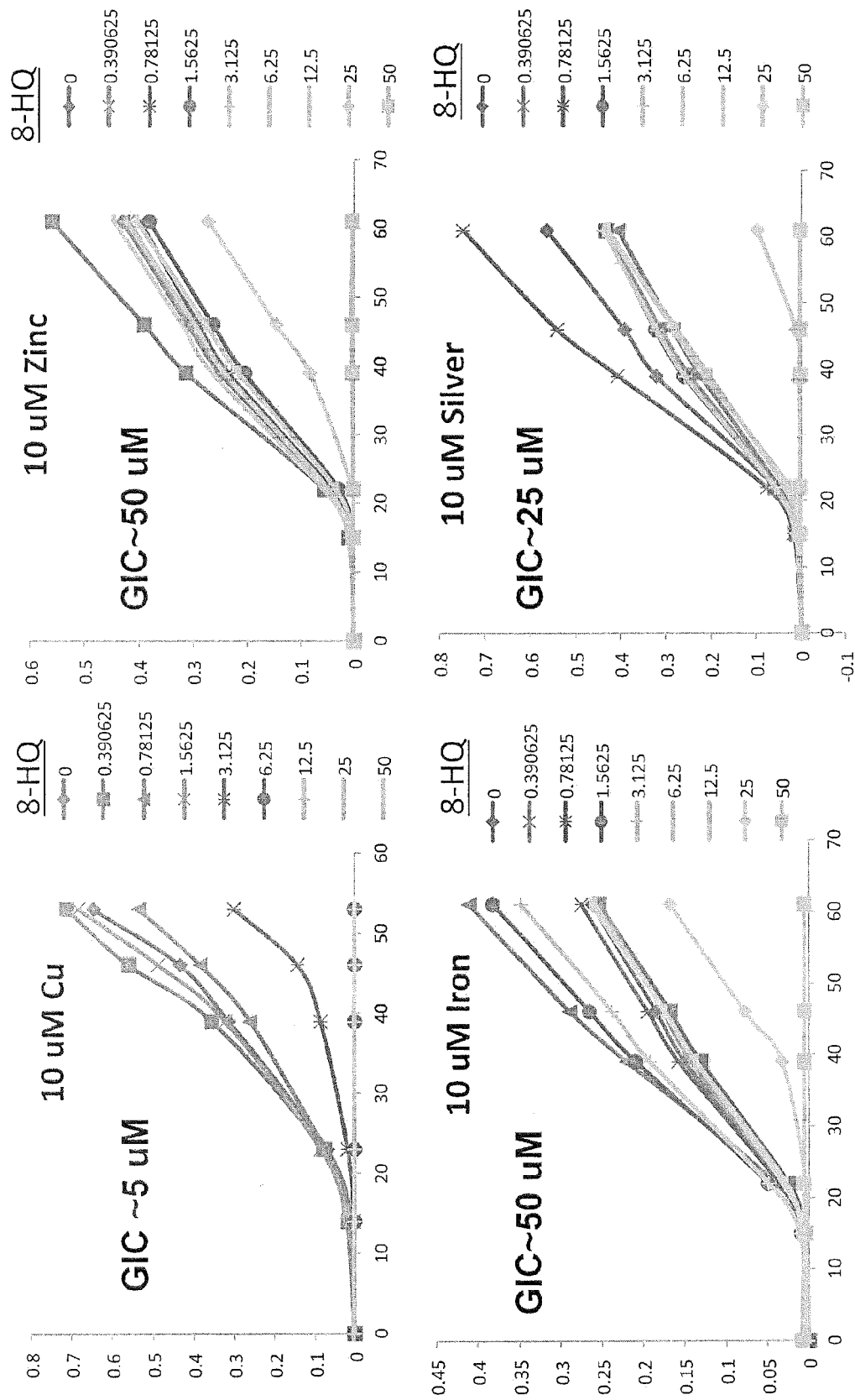
FIG. 3 is a graph showing the minimum inhibitory concentration (MIC) for Cu. The ability of 8-HQ to inhibit C. neoformans growth was tested with respect to metal specificity. The concentration of the indicated metals was held constant at 10 μM and cells were incubated in the presence of escalating doses of 8HQ from 0 to 50 μM. Growth was monitored over a time course in hours (x-axis) and the optical density at 600 nm was plotted at each time (y-axis). From these data the Minimum Inhbitory Concentration (MIC) of 8HQ was determined for each condition as the concentration of 8HQ required to completely inhibit C. neoformans growth.

In accord with its known antifungal activity, we found that 8HQ inhibited growth of *C. neoformans* in a Cu-dependent manner. (FIG. 2). Further studies counting colony-forming units (cfu) indicated that inhibition was fungicidal, not just fungistatic (FIG. 2). The Minimum Inhibitory Concentration (MIC) was defined as the concentration of 8HQ required to completely inhibit *C. neoformans* growth in the presence of 10 μM supplemental metal. The MIC for Cu was found to be 5 μM, but it was 50 μM for iron and zinc and 25 μM for silver (FIG. 3). These results indicate that the fungicidal effect of 8HQ is distinct to Cu.

While the fungistatic property of 8HQ and Cu is promising in terms of an antimicrobial agent, we note that 8HQ also showed Cu-dependent cytotoxicity against mammalian cells, a disadvantage in terms of developing a drug for human use. The results are shown as blue bars in FIG. 3 for cell viability of macrophage-like murine J774A.1 cells, where an IC$_{50}$ value for 8HQ was ~5 μM but decreased to sub-μM in medium supplemented with 10 μM CuSO$_4$. We found similar results in IFN-γ and LPS-activated primary bone marrow derived macrophage cells (BMM) from A/J mice.

While the cytotoxic mechanism of action of 8HQ may be multifaceted, its ionophore properties that enable it to translocate Zn$^{2+}$ and Cu$^{2+}$ across cell membranes as neutral, lipohilic metal complexes independent of metal pumps and transporters has been well documented.[23, 24] If Cu binding and translocation are critical for the cytotoxicity we observe for 8HQ in mouse macrophage cells and in *C. neoformans*, then blocking the metal binding site of 8HQ should abrogate its toxicity. Consistent with this hypothesis, 6-hydroxyquinoline (6HQ, an isomer of 8HQ that cannot form a bidentate chelate ring with metal cations) does not inhibit growth of *C. neoformans*, even in the presence of 1 mM CuSO$_4$ (Table). Likewise, the prochelator QBP is also nontoxic to *C. neoformans* up to the 100 μM dose tested, even in the presence of 1 mM CuSO$_4$. These results highlight the synergistic requirement for both Cu and the metal-binding functionality of 8HQ to kill *C. neoformans*.

TABLE 1

Comparison of the MIC values for 8HQ, 6HQ, and QBP with and without supplemental Cu, for the growth inhibition of *C. neoformans*.

|  | 8HQ | 6HQ | QBP |
|---|---|---|---|
| MIC (no Cu added) | >100 μM | >100 μM | >100 μM |
| MIC (with added Copper(II) Sulfate) | 5 μM * 10 M $Cu^{2+}$ | >100 μM * 1 mM $Cu^{2+}$ | >100 μM * 1 mM $Cu^{2+}$ |

Figure 4:
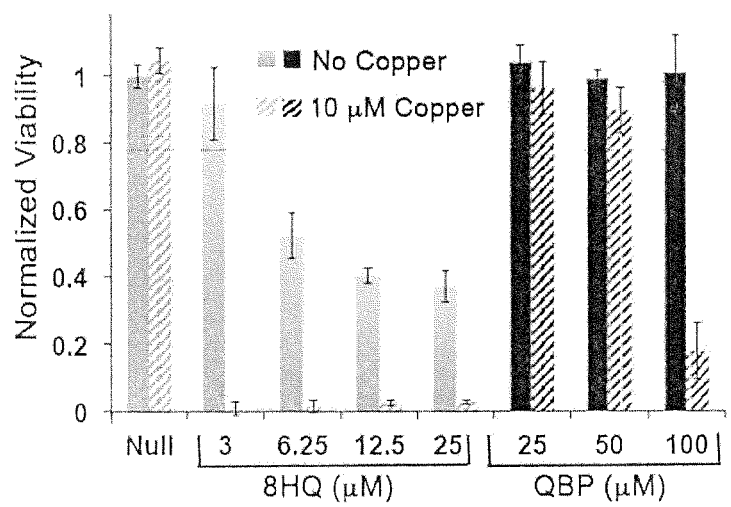
FIG. 4 is a graph showing 8HQ, not QBP, toxic to mammalian cells. Diminished viability of murine macrophage-like J774.1 cells upon treatment with 8HQ is exacerbated by supplemental Cu. The only treatment with prochelator QBP that causes loss of viability is at the highest dose (100 μM) with supplemental Cu, likely the result of in-situ conversion from QBP to 8HQ under these conditions. Cells were seeded at $1\times10^5$ cells/mL in 96-well plate in DMEM+10% FBS, incubated at 37° C. for 12 h, and assayed for viability with CellTiter-Glo®.

3. Chelator 8HQ is Cytotoxic to Mammalian Cells, But Prochelator QBP is Not. Consistent with its inability to bind Cu, our prochelator QBP was nontoxic to J774A.1 (FIG. 4), BMM (data not shown) and *C. neoformans* (FIG. 5) at doses up to 50-100 μM, even with supplemental Cu. The lack of cytotoxicity of QBP contrasts sharply with the Cu-stimulated toxicity of micromolar 8HQ.

Figure 5:
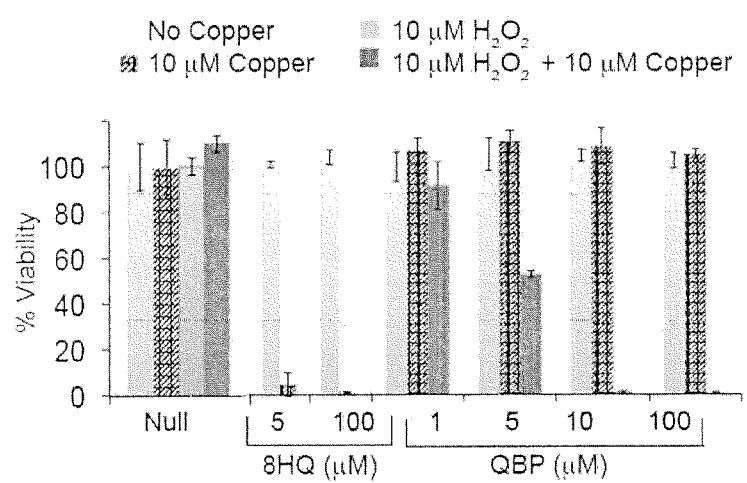
FIG. 5 is a graph showing the effects of Cu, $H_2O_2$ with 8HQ/QBP on C. neoformans. WT C. neoformans H99 strain was grown in SC media+/−10 μM CuSO4 and 8HQ or QBP at indicated concentrations. Growth was monitored by OD600 and normalized to 100% viability for untreated controls after 50 h at 30° C. 8HQ+Cu inhibits growth, while QBP requires stimulatory $H_2O_2$ to have an effect, consistent with prochelator-to-chelator conversion under these conditions.

4. Toxicity of Prochelator is Activated by $H_2O_2$. In vitro, QBP converts cleanly to 8HQ upon reaction with $H_2O_2$ with a rate constant of 0.25 $M^{-1}s^{-1}$ at 25° C.[25] To test whether this reactivity translates to a change in cytotoxicity, we repeated the *C. neoformans* growth assays of 8HQ and QBP with $H_2O_2$, a known component of the oxidative burst generated in phagosomes of activated macrophages.[26, 27] As shown in FIG. 5, the combination of Cu and $H_2O_2$ did not inhibit cell growth, nor did the combination of prochelator QBP and Cu, but the trifecta of QBP/$H_2O_2$/Cu inhibited cell growth as well as 8HQ/Cu. The in vitro rate constant correlates reasonably well with this result, and suggests that submicromolar released 8HQ is sufficient to prevent growth when Cu is present. Furthermore, fluorescent boronate-based probes with similar rate constants to QBP for peroxide activation have been shown to detect $H_2O_2$ in activated macrophages,[26] suggesting that endogenously generated $H_2O_2$ during an immune response will be sufficient for triggering our prochelators. These results lend support to our central hypothesis that small molecules can be switched on by chemical triggers associated with the immune response to induce Cu-dependent toxicity. Notably, intraperitoneal administration of either 2 mg/kg or 10 mg/kg QBP to mice every second day, over a two-week period, showed no obvious adverse affects.

Figure 6:
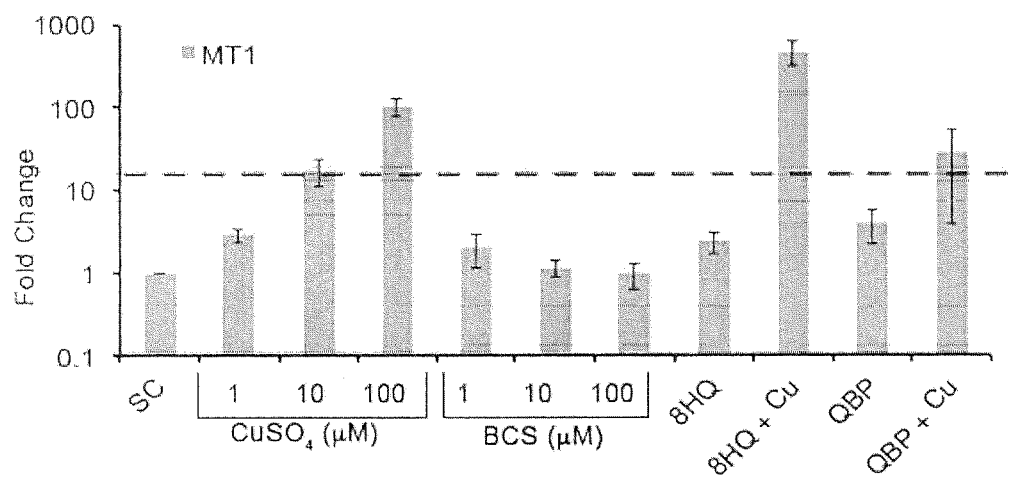
FIG. 6 is a graph showing Cu+8HQ (not QBP) increase expression levels of the MT1 gene. An overnight growth of WT C. neoformans was diluted in SC media to an $OD_{600}$ of 0.2, incubated for 3 h to begin log phase growth, and treated with Cu and/or compound as indicated. After 30 min, cells were harvested and RNA was extracted, with subsequent RT-PCR to produce cDNA. Fold-change of MT1 was quantified using qPCR and normalized to ACT1. The strength of MT1 induction increases with [Cu]. As a control, the extracellular $Cu^+$ chelator BCS does not lead to a change in MT1 expression. 8HQ and QBP (10 μM) alone do not cause robust induction of MT1, while 8HQ+Cu (10 pM each) leads to MT1 levels greater than what is seen with 100 μM CuSO4 alone. In comparison, C. neoformans treated with QBP+Cu (10 μM each) responds identically to treatment with 10 μM CuSO4 alone. These data suggest that 8HQ elevates bio-available intracellular Cu levels in WT C. neoformans cells, while the unactivated prochelator QBP does not influence the cellular response to Cu.

5. 8HQ Increases the Cu Burden on *C. neoformans*. Our working hypothesis for the mechanism of action of 8HQ is that it increases the microbial burden of bioreactive Cu. If 8HQ translocates Cu into the cell in a bioavailable form, we would expect expression levels of proteins involved in Cu homeostasis to be sensitive to that influx. Indeed, data in FIG. 6 show that metallothionein 1 (MT1) is hyper-activated within 30 min of exposure to 8HQ+Cu. Metallothionein proteins are known to detoxify Cu and other metals by encasing them within cysteine-rich coordination sites. Increased expression of MT1 is consistent with our hypothesis that 8HQ increases bioavailable Cu, which is sensed by the cell in the form of MT1 transcription.

Figure 7:
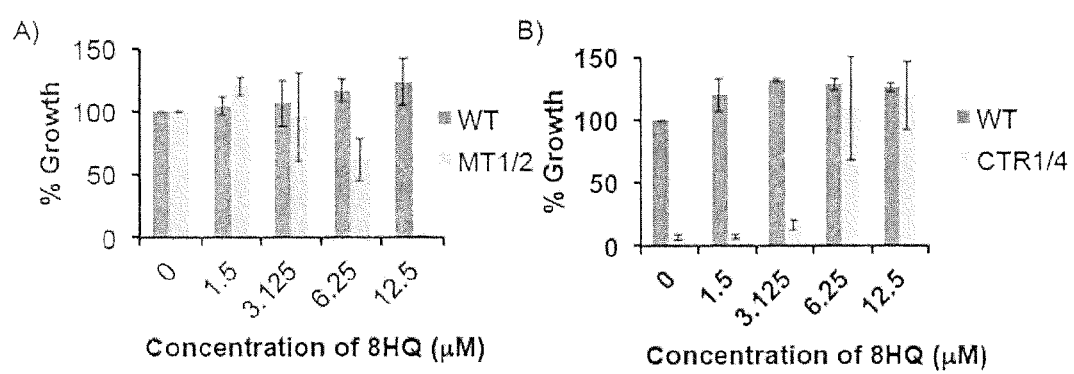
FIG. 7 is a graph showing the Effects of 8HQ on growth of C. neoformans mutants. A) WT C. neoformans and a MT1/2Δ☐☐, strain were grown in SC media with 10 μM CuSO4 and increasing [8HQ]. Suggestive of 8HQ promoting Cu toxicity, the mutant strain unable to produce metallothioneins shows a growth defect beginning at 6.25 μM 8HQ in these conditions. B) Conversely, the CTR1/4Δ strain is unable to grow in YPEG media without Cu supplementation as this strain is unable to acquire Cu. Addition of 8HQ promotes growth of the transporter mutant, suggesting that 8HQ is able to transfer trace Cu from the media into the cells.

Additional support for the overall hypothesis that 8HQ increases cellular Cu independently from normal biological uptake pathways comes from testing the effects of Cu and 8HQ on mutant strains of *C. neoformans* that are deficient in various Cu homeostasis proteins. The metallothionein1/2 (MT1/2) double knock out strain is exceedingly sensitive to Cu+8HQ treatment (FIG. 7A), consistent with the hypothesis that MTs are required to detoxify Cu. In contrast, the Ctrl/4 double knock out strain cannot grow on YPEG (complete ethanol-glycerol) media because of the severe Cu deficiency created by the absence of both Cu import proteins Ctrl and Ctr4; however, treatment with 8HQ overrides this deficiency to recover growth, even without supplemental Cu added to the media (FIG. 7B).

Figure 8:
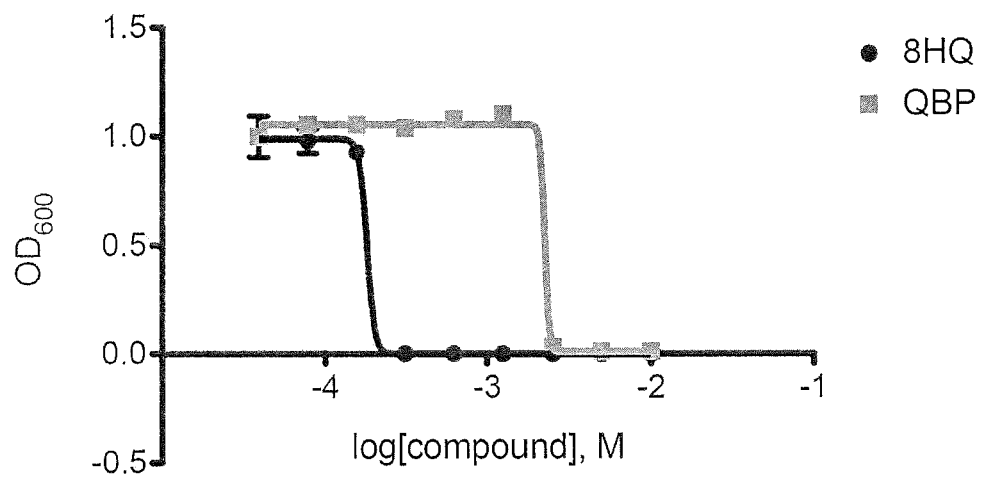
FIG. 8 is a graph showing that S. Aureus dose response to 8HQ and QBP. Under these conditions, 8HQ inhibits S. Aureus growth at concentrations above ~150 μM, whereas QBP in nontoxic up to ~2.5 mM. Supplemental Cu was not added in these experiments, so presumably 8HQ is using Cu present in the tryptic soy broth medium.
Figure 9:
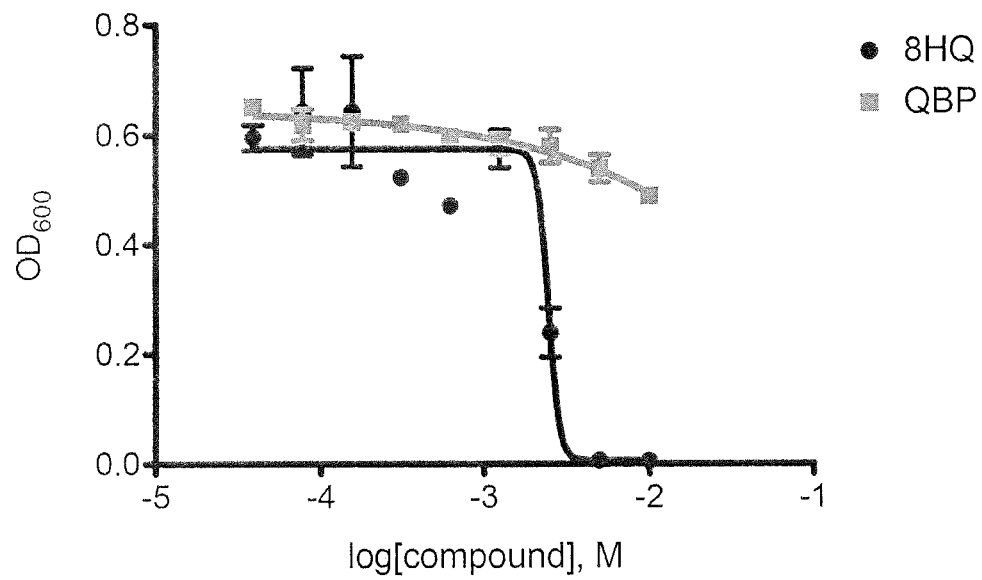
FIG. 9 is a graph showing that E. coli dose response to 8HQ and QBP. Under these conditions, 8HQ inhibits E. coli growth at concentrations above ~1.5 mM, whereas QBP in nontoxic up to 10 mM. Supplemental Cu was not added in these experiments, so presumably 8HQ is using Cu present in the M9 minimal medium.

6. Broad Spectrum Activity The antimicrobial properties of oxine (8HQ) against a broad spectrum of fungal and bacterial pathogens has long been recognized. Taking advantage of this cytotoxic activity while minimizing damage to the host has prevented the application of these compounds to combat infectious disease in humans. The common response of macrophages to induce an oxidative burst against a broad spectrum of invading pathogens suggests that the prochelator QBP may provide a broad spectrum antimicrobial that will be unleashed as a result of this common immune response. We tested this hypothesis by comparing the cytotoxicity of 8HQ vs QBP against other microbes. Preliminary results indeed show a differential cytotoxicy of 8HQ vs QBP in *S. aureus* (FIG. 8), *E. coli* (FIG. 9) and *M. marinum* (data not shown). In these preliminary results, supplemental Cu was not added to the growth media, so presumably 8HQ uses the basal Cu present in the media to inflict its growth inhibitory action. The fact that QBP was significantly less toxic to all these microbes is consistent with our hypothesis that it could be converted to a toxic agent upon reaction with ROS to generate 8HQ.

REFERENCES

1. Thi, E. P.; Lambertz, U.; Reiner, N. E., Sleeping with the Enemy: How Intracellular Pathogens Cope with a Macrophage Lifestyle. *PLoS Pathog* 2012, 8, el 002551.

2. Nathan, C.; Shiloh, M. U., Reactive oxygen and nitrogen intermediates in the relationship between mammalian hosts and microbial pathogens. *Proc. Natl Acad. Sci. USA* 2000, 97, 8841-8848.
3. Borkow, G.; Gabbay, J., Copper as a Biocidal Tool. *Curr. Med. Chem.* 2005, 12, 2163-2175.
4. Milanino, R.; Buchner, V., Copper: Role of the 'Endogenous' and 'Exogenous' Metal on the Development and Control of Inflammatory Processes. In Reviews on Environmental Health, 2006; Vol. 21, p 153.
5. Percival, S. S., Copper and immunity. *Am. J. Clin. Nutr* 1998, 67, 1064S-1068S.
6. Hodgkinson, V.; Petris, M. J., Copper Homeostasis at the Host-Pathogen Interface. *J. Biol. Chem.* 2012, 287, 13549-13555.
7. White, C.; Lee, J.; Kambe, T.; Fritsche, K.; Petris, M. J., A Role for the ATP7A Copper-transporting ATPase in Macrophage Bactericidal Activity. *J. Biol. Chem.* 2009, 284, 33949-33956.
8. Solioz, M.; Abicht, H. K.; Mermod, M.; Mancini, S., Response of Gram-positive bacteria to copper stress. *J. Biol. Inorg. Chem.* 2010, 15, 3-14.
9. Dollwet H. H. A.; J., S. J. R., Historic uses of copper compounds in medicine. *Trace Elem. Med.* 1985, 2, 80-87.
10. Casey, A. L.; Adams, D.; Karpanen, T. J.; Lambert, P. A.; Cookson, B. D.; Nightingale, P.; Miruszenko, L.; Shillam, R.; Christian, P.; Elliott, T. S. J., Role of copper in reducing hospital environment contamination. *J. Hosp. Infect.* 2010, 74, 72-77.
11. Mikolay, A.; Huggett, S.; Tikana, L.; Grass, G.; Braun, J.; Nies, D., Survival of bacteria on metallic copper surfaces in a hospital trial. *Appl. Microbiol. Biotechnol.* 2010, 87, 1875-1879.
12. Dupont, C. L.; Grass, G.; Rensing, C., Copper toxicity and the origin of bacterial resistance-new insights and applications. *Metallomics* 2011.
13. Lin, X.; Heitman, J., The Biology of the *Cryptococcus neoformans* Species Complex. *Annual Review of Microbiology* 2006, 60, 69-105.
14. Kronstad, J.; Saikia, S.; Nielson, E. D.; Kretschmer, M.; Jung, W.; Hu, G.; Geddes, J. M. H.; Griffiths, E. J.; Choi, J.; Cadieux, B.; Caza, M.; Attarian, R., Adaptation of *Cryptococcus neoformans* to Mammalian Hosts: Integrated Regulation of Metabolism and Virulence. *Eukaryotic Cell* 2012, 11, 109-118.
15. Block, S. S., Fungitoxicity of 8-Quinolinols. *J. Agric. Food. Chem.* 1955, 3, 229-234.
16. Nicoletti, G.; Domalewska, E.; Borland, R., Fungitoxicity of oxine and copper oxinate: effects of pH, metals and chelating agents on activity. *Mycolog. Res.* 1999, 103, 1085-1097.
17. Gershon, H.; Parmegiani, R.; Nickerson, W. J., Antimicrobial Activity of Metal Chelates of Salts of 8-Quinolinols with Aromatic Hydroxycarboxylic Acids. *App. Microbiol.* 1962, 10, 556-560.
18. Adlard, P. A.; Cherny, R. A.; Finkelstein, D. I.; Gautier, E.; Robb, E.; Cortes, M.; Volitakis, I.; Liu, X.; Smith, J. P.; Perez, K.; Laughton, K.; Li, Q.-X.; Charman, S. A.; Nicolazzo, J. A.; Wilkins, S.; Deleva, K.; Lynch, T.; Kok, G.; Ritchie; C. W.; Tanzi, R. E.; Cappai, R.; Masters, C. L.; Barnham, K. J.; Bush, A. I., Rapid Restoration of Cognition in Alzheimer's Transgenic Mice with 8-Hydroxy Quinoline Analogs Is Associated with Decreased Interstitial A[beta]. *Neuron* 2008, 59, 43-55.
19. Tateishi, J., Subacute myelo-optico-neuropathy: Clioquinol intoxication in humans and animals. *Neuropathology* 2000, 20, 20-24.
20. Bareggi, S. R.; Cornelli, U., Clioquinol: Review of its Mechanisms of Action and Clinical Uses in Neurodegenerative Disorders. *CNS Neuroscience & Therapeutics* 2010, no-no.
21. Benvenisti-Zarom, L.; Chen, J.; Regan, R. F., The oxidative neurotoxicity of clioquinol. *Neuropharmacology* 2005, 49, 687-694.
22. Hindo, S. S.; Mancino, A. M.; Braymer, J. J.; Liu, Y; Vivekanandan, S.; Ramamoorthy, A.; Lim, M. H., Small Molecule Modulators of Copper-Induced Aβ3 Aggregation. *J Am. Chem. Soc.* 2009, 131, 16663-16665.
23. Li, C.; Wang, J.; Zhou, B., The Metal Chelating and Chaperoning Effects of Clioquinol: Insights from Yeast Studies. *Journal of Alzheimer's Disease* 2010, 21, 1249-1262.
24. Zhai, S.; Yang, L.; Cui, Q.; Sun, Y; Dou, Q.; Yan, B., Tumor cellular proteasome inhibition and growth suppression by 8-hydroxyquinoline and clioquinol requires their capabilities to bind copper and transport copper into cells. *J Biol. Inorg. Chem.* 2010, 15, 259-269.
25. Dickens, M. G.; Franz, K. J., A Prochelator Activated by Hydrogen Peroxide Prevents Metal-Induced Amyloid β Aggregation. *ChemBioChem* 2010, 11, 59-62.
26. Srikun, D.; Miller, E. W.; Domaille, D. W.; Chang, C. J., An ICT-Based Approach to Ratiometric Fluorescence Imaging of Hydrogen Peroxide Produced in Living Cells. *J. Am. Chem. Soc.* 2008, 130, 4596-4597.
27. VanderVen, B. C.; Yates, R. M.; Russell, D. G., Intraphagosomal Measurement of the Magnitude and Duration of the Oxidative Burst. *Traffic* 2009, 10, 372-378.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods described herein are presently representative of preferred embodiments, are exemplary, and are not intended as limitations on the scope of the invention. Changes therein and other uses will occur to those skilled in the art which are encompassed within the spirit of the invention as defined by the scope of the claims.

We claim:

1. A method of treating pathogenic infections in a subject comprising administering to the subject a therapeutically effective amount of a prochelator such that the infection is treated, wherein the pathogenic infection comprises a pathogen, wherein the pathogen is fungal or bacterial, wherein said prochelator is a compound of Formula II:

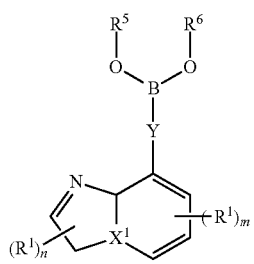

(II)

wherein:
Y is a covalent bond or —O—$R^7$—$R^8$—, where $R^7$ is —$CH_2$— or —$CO_2CH_2$— and $R^8$ is phenylene;
n and m are each an integer from 1 to 3;
each $R^1$ is independently selected from the group consisting of: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy;
$R^5$ and $R^6$ are independently selected H, alkyl, or haloalkyl, or together form an alkylene bridge, which alkylene bridge may be unsubstituted or substituted from 1 to 4 times with alkyl, halo, cycloalkyl, aryl, a fused cycloalkyl or a fused aryl ring;
each X is independently selected from the group consisting of N, O, and CH; and
dashed lines represent optional double bonds;
or a pharmaceutically acceptable salt or prodrug thereof.

2. The method of claim 1, wherein Y is a covalent bond or —O—$R^7$—$R^8$—, where $R^7$ is —$CH_2$— or —$CO_2CH_2$— and said $R^8$ phenylene is unsubstituted or substituted from 1 to 4 times with independently selected halo or alkyl.

3. The method of claim 1, wherein $R^5$ and $R^6$ are independently selected H, alkyl, or haloalkyl.

4. The method of claim 1, wherein $R^5$ and $R^6$ together form an alkylene bridge, which alkylene bridge may be unsubstituted or substituted from 1 to 4 times with alkyl, halo, cycloalkyl, aryl, a fused cycloalkyl or a fused aryl ring.

5. The method of claim 1, wherein $R^5$ and $R^6$ together form a C2 alkylene bridge having a bicyclic cycloalkyl substituted thereon, which C2 alkylene bridge and/or bicyclic cycloalkyl may be unsubstituted or substituted from 1 to 4 times with alkyl or halo.

6. The method as in claim 1, wherein the fungal pathogen comprises a yeast.

7. The method as in claim 6, wherein the yeast comprises *C. neoformans*.

8. The method as in claim 1, wherein the bacterial pathogen comprises a gram-negative bacteria.

9. The method as in claim 8, wherein the gram-negative bacteria comprises *E. coli*.

10. The method as in claim 1, wherein the bacterial pathogen comprises a gram-positive bacteria.

11. The method as in claim 10, wherein the gram-positive bacteria is selected from the group consisting of *S. aureus* and *Mycobacterium*.

12. The method according to claim 10, wherein the gram-positive bacteria comprises *S. aureus*.

13. The method as in claim 11, wherein the *Mycobacterium* comprises *M. tuberculosis*, *M. marinum*, or *M.leprae*.

14. The method of claim 1, wherein the prochelator is administered either at the onset of disease, prior to disease symptoms or after the onset of disease symptoms.

15. The method of claim 1, wherein a subject is a mammal.

16. The method as in claim 13, wherein the subject is human.

17. The method of claim 1, wherein $R^5$ and $R^6$ together form a group:

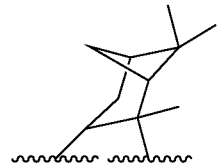

18. The method of claim 17, wherein:
Y is a covalent bond;
n and m are each 1;
each $R^1$ is H; and
$X^1$ is CH;
or a pharmaceutically acceptable salt thereof.

* * * * *

UNITED STATES PATENT AND TRADEMARK OFFICE
CERTIFICATE OF CORRECTION

PATENT NO.         : 9,526,740 B2                                        Page 1 of 1
APPLICATION NO.    : 15/094349
DATED              : December 27, 2016
INVENTOR(S)        : Franz et al.

It is certified that error appears in the above-identified patent and that said Letters Patent is hereby corrected as shown below:

In the Specification

Column 3, Line 63: Please correct "10pM" to read -- 10µM --

In the Claims

Column 20, Claim 1, Line 66: Please correct "bacterial, wherein" to read -- bacterial, and wherein --

Signed and Sealed this
Fourth Day of July, 2017

Joseph Matal
*Performing the Functions and Duties of the*
*Under Secretary of Commerce for Intellectual Property and*
*Director of the United States Patent and Trademark Office*